US010813366B2

(12) United States Patent
Murphy et al.

(10) Patent No.: US 10,813,366 B2
(45) Date of Patent: Oct. 27, 2020

(54) *BIFIDOBACTERIUM LONGUM* NCIMB 41676

(71) Applicants: PrecisionBiotics Group Limited, Cork (IE); University College Cork—National University of Ireland, Cork, Cork (IE)

(72) Inventors: Eileen Frances Murphy, Cork (IE); David Groeger, Cork (IE); Timothy Dinan, Cobh (IE); John Cryan, Cork (IE)

(73) Assignees: PrecisionBiotics Group Limited, Cork (IE); University College Cork—National University of Ireland, Cork, Cork (IE)

( * ) Notice: Subject to any disclaimer, the term of this patent is extended or adjusted under 35 U.S.C. 154(b) by 0 days.

(21) Appl. No.: 16/794,019

(22) Filed: Feb. 18, 2020

(65) Prior Publication Data

US 2020/0214308 A1 Jul. 9, 2020

Related U.S. Application Data

(63) Continuation of application No. PCT/EP2019/052140, filed on Jan. 29, 2019.

(30) Foreign Application Priority Data

Jan. 29, 2018 (EP) ..................................... 18153997

(51) Int. Cl.
*A61K 35/745* (2015.01)
*A23L 33/135* (2016.01)
*A23L 33/00* (2016.01)
*A23C 9/123* (2006.01)
*C12R 1/01* (2006.01)

(52) U.S. Cl.
CPC .......... *A23C 9/1234* (2013.01); *A23L 33/135* (2016.08); *A23L 33/40* (2016.08); *C12R 1/01* (2013.01)

(58) Field of Classification Search
None
See application file for complete search history.

(56) References Cited

U.S. PATENT DOCUMENTS 10,144,978 B2   12/2018   O'Mahony et al.
2018/0282825 A1  10/2018   O'Mahony et al.

FOREIGN PATENT DOCUMENTS

| JP | 2007169200 A | 5/2007 |
| JP | 2017081853 A | 5/2017 |
| WO | WO 2010/055499 A2 | 5/2010 |
| WO | WO 2010/055499 A3 | 5/2010 |
| WO | WO 2010/060722 A1 | 6/2010 |
| WO | WO 2011/058535 A1 | 5/2011 |
| WO | WO 2015/146844 A1 | 1/2015 |
| WO | WO 2018/002238 A1 | 1/2018 |
| WO | WO 2018/002240 A1 | 1/2018 |

OTHER PUBLICATIONS

Allen, A.P. et al., "Bifidobacterium Longum 1714 as a Translational Psychobiotic: Modulation of Stress, Electrophysiology and Neurocognition in Healthy Volunteers", *Translational Psychiatry*, 6, e939 (2016).
Allen, A.P. et al., "Bifidobacterium Longum 1714: A Psychobiotic That Modulates Brian Activity, The Stress Response and Neurocognitive Performance in Healthy Volunteers", (2015).
Bravo, Javier A. et al., "Ingestion of *Lactobacillus* Strain Regulates Emotional Behavior and Central GABA Receptor Expression in a Mouse Via The Vagus Nerve", *PNAS*, vol. 108, No. 38, pp. 16050-16055, (2011).
Buysse, Daniel J., et al., "Quantification of Subjective Sleep Quality in Healthy Elderly Men and Women Using The Pittsburgh Sleep Quality Index (PSQI)", *Sleep*, 14 (4): pp. 331-38, (1991).
Buysse, Daniel J., et al., "The Pittsburgh Sleep Quality Index: A New Instrument for Psychiatric Practice and Research", *Psychiatry Research*, 28, pp. 193-213, (1988).
Colten, Harvey R., et al., "Sleep Disorders and Sleep Deprivation: An Unmet Public Health Problem", *The National Academies Press*, (2006).
Dinan, Timothy G., et al., "Psychobiotics: A Novel Class of Psychotropic", *Science Diet*, Biological Psychiatry, vol. 74, Issue 10, pp. 720-726, (2013).
Fillingim, Roger B., et al., "Potential Psychosocial Risk Factors for Chronic TMD: Descriptive Data and Empirically Identified Domains From The OPPERA Case-Control Study", *Journal Pain*, (2012).
Herman, C.R., et al., "The Effectiveness of Adding Pharmacologic Treatment With Clonazepam or Cyclobenzaprine to Patient Education and Self-Care for The Treatment of Jaw Pain Upon Awakening: A Randomized Clinical Trial", *Journal Orofac Pain*, 16(1) pp. 64-70, Winter (2002).
Health and Nutritional Properties of Probiotics in *Food Including Powder Milk with Live Lactic Acid Bacteria*, (2001).
International Search Report for PCT/EP2019/051240 dated May 15, 2019 (4 pages).
Jay, et al., "Modern Food Microbiology", 7th edition, (2005).
Kazemi, A. et al., "Effect of Probiotic and PreBiotic vs Placebo on Psychological Outcomes in Patients With Major Depressive Disorder: A Randomized Clinical Trial", *Clinical Nutrition*, (2018), https://doi.org/10.1016/j.clnu.2018.04.010.
Kell, Douglas B. et al., "Viability and Activity in Readily Culturable Bacteria: A Review and Discussion of the Practical Issues", https://link.springer.com/article/10.1023/A:1000664013047.
Mairesse, J. et al., "Lactobacillus Reuteri DSM 17938 and Bifidobacterium Longum Atcc BAA-999 Normalize Sleep Patterns in Prenatal Stress Rats", *Human Physiology and Pharmacology, University of Rome*, p. 797 (2011).

(Continued)

*Primary Examiner* — Sarvamangala Devi
(74) *Attorney, Agent, or Firm* — Bookoff McAndrews, PLLC

(57) ABSTRACT

Methods of treating a subject by administering *Bifidobacterium longum* strain NCIMB 41676 are discussed. The method may include orally administering a formulation comprising *Bifidobacterium longum* strain NCIMB 41676 to improve sleep.

25 Claims, 8 Drawing Sheets

(56) References Cited

OTHER PUBLICATIONS

Pinto-Sanchez, Maria Ines et al., "Probiotic Bifidobacterium Longum NCC3001 Reduces Depression Scores and Alters Brain Activity: A Pilot Study in Patients With Irritable Bowel Syndrome", *Gastroenterology*, (2017).

Porto, Felipe et al., "Differences in Psychosocial Functioning and Sleep Quality Between Idiopathic Continuous Orofacial Neuropathic Pain Patients and Chronic Masticatory Muscle Pain Patients", *Journal of Orofacial Pain*, vol. 25 Issue 2, pp. 117-124 (2011).

Savignac, H.M. et al., "Bifidobacteria Exert Strain-Specific Effects on Stress-Related Behavior and Physiology in BALB/c Mice", *Neurogastroenterology & Motility*, 26, pp. 1615-1627 (2014).

Savignac, H.M. et al., Bifidobacteria Modulate Cognitive Processes in an Anxious Mouse Strain, *Behavioural Brain Research*, 287, pp. 59-72 (2015).

U.S. Appl. No. 16/789,768, filed Feb. 13, 2020.

Wang, "Effects of Probiotics on Central Nervous System Functions in Humans", pp. 1-152 (2017).

'COMBO' product: *B. longum* 35624 + *B. longum* 1714

Q6 During the past month, how would you rate your sleep quality overall:

Minimum Score = 0 (better); Maximum Score = 3 (worse)

| Sleep Quality | Week 0 | Week 4 | Week 8 | Week 12 | Week 16 |
|---|---|---|---|---|---|
| Very bad | 3% | 3% | 5% | 8% | 3% |
| Fairly bad | 38% | 28% | 28% | 30% | 28% |
| Fairly good | 48% | 48% | 48% | 53% | 53% |
| Very good | 8% | 25% | 25% | 18% | 20% |

N=40

BIFIDOBACTERIUM LONGUM NCIMB 41676

CROSS-REFERENCE TO RELATED APPLICATIONS

This is a continuation of International Application No. PCT/EP2019/052140, filed on Jan. 29, 2019, incorporated by reference herein in its entirety, which claims the benefit of priority of European Application No. 18153997.4, filed Jan. 29, 2018.

INTRODUCTION

Accumulating data indicate that the gut microbiota communicates with the central nervous system (CNS), the part of the nervous system consisting of the brain and spinal cord,—possibly through neural, endocrine and immune pathways—and thereby influences brain function and behaviour (Dinan et al., 2013; Bravo et. al, 2011). Probiotics are defined as live bacteria, which when ingested in adequate amounts, confer a health benefit (WHO, 2001). Recent evidence suggests that probiotics may have a role in mental health and well-being (Dinan et al., 2013). However, while there is increasing interest in this field and preclinical trials show promising results, this field is in its infancy and very little is known about the effect of probiotic on mental well-being in humans.

Sleep is vital for normal physiological and psychological functioning. Unfortunately, 50-70 million Americans experience disordered sleep, inflicting substantial financial and societal cost (Institute of Medicine Committee on Sleep & Research, 2006). Sleep disturbance is a significant stressor that contributes to cognitive impairment, affective disruption and physical disease Modern lifestyles contribute to this growing health concern by shifting importance away from healthy sleep habits and towards other activities. Developing effective and safe treatments for disturbed sleep is a necessary public priority.

Pharmaceutical sleep aids, like most pharmaceutical treatments, can have harmful side effects. Psychological treatments are generally side-effect free but require substantial time and effort.

Probiotics may have considerable clinical utility in helping address disrupted sleep. However, the relationship between probiotics and sleep is still poorly understood and no studies have reported assessing the effects on sleep in humans of a *Bifidobacterium longum* strain.

WO2010/0606722 A1 reported, based on testing with mice, that a *Bifidobacterium longum* BAA-999 may improve sleep quality and reduce the number of episodes of wakefulness in infants, and hypothesised that this was due to possible anxiolytic effects in humans. However, as reported in Pinto-Sanchez et al., 2017(3) further work in humans did not support this anxiolytic effect.

There is a need for a probiotic which is effective in improving sleep quality.

STATEMENTS OF INVENTION

The invention also provides *Bifidobacterium longum* strain NCIMB 41676 for use in improving sleep in humans.

According to the invention there is provided *Bifidobacterium longum* strain NCIMB 41676 for use in improving sleep quality in humans.

According to the invention there is provided *Bifidobacterium longum* strain NCIMB 41676 for use in improving sleep quality in mammals.

According to the invention there is provided *Bifidobacterium longum* strain NCIMB 41676 for use in improving sleep in mammals.

The *Bifidobacterium* strain NCIMB 41676 may be in the form of viable cells.

The *Bifidobacterium* strain NCIMB 41676 may be in the form of non-viable cells.

The *Bifidobacterium* strain NCIMB 41676 may be present in the formulation in an amount of more than $10^6$ cfu, typically from $10^7$ to $10^{10}$, typically from $10^8$ to $10^9$ cfu. In one case the *Bifidobacterium* strain NCIMB 41676 is present in the formulation in an amount of about $1\times10^9$ cfu.

Bacterial viability reflects the number of culturable bacteria within a sample, i.e. the number of bacteria which retain the ability to reproduce when grown under optimal conditions (Viable cells). Put another way viability reflects the number of individual bacterial cells which retain the ability to replicate into larger bacterial colonies (colony forming units (CFUs)).

Viability is commonly determined using plate-counting methods, whereby a bacterial sample is diluted and then incubated on an agar plate containing the necessary nutrients for growth. Viability is then calculated from the number of bacterial colonies identified on a plate. Such methods are summarized in Modern Food Biology 2005 $7^{th}$ edition, James Monroe Jay, Martin J. Loessner, David A. Golden, Springer Science, New York.

Whilst plate-counting gives a good indication of viability, it does not encompass all living bacterial cells in the sample. (Kell, Douglas B., et al. "Viability and activity in readily culturable bacteria: a review and discussion of the practical issues." *Antonie van Leeuwenhoek* 73.2 (1998): 169-187).

Samples will also contain "viable but non-culturable" (VBNC) cells which remain metabolically active but have lost the ability to replicate at the time of analysis by plate count, and thus despite being alive will not form CFUs. Finally, samples will also contain dead cells. These two groups can be grouped together as "Non-Viable cells". Therefore Non-viable cells are the inverse of Viable cells i.e. all those cells which have lost the ability to replicate when tested.

All samples containing Viable cells will also contain Non-Viable cells, therefore the definition of a Viable cell culture is clarified using CFU measurements.

All Non-Viable samples will contain at least VNBCs and possibly small amounts of Viable cells. Industry standard lower level detection limits of $10^3$ CFU/g viable cells allow for the inherent process variability caused by the presence of a certain number of VBNCs/Viable cells in Non-Viable samples.

In some embodiments, such as, but not limited to, special sterile food products or medicaments a non-replicating form of a probiotic strain may be preferable. For example, at least 95%, preferably at least 97%, more preferably at least 99% of the *Bifidobacteria* strain can be non-replicating in the composition.

In some embodiments the formulation is in the form of a bacterial broth.

In some cases the formulation in the form of a freeze dried powder.

The formulation may further comprise a prebiotic material.

In some cases the formulation further comprises an ingestible carrier. The ingestible carrier may be a pharmaceutically acceptable carrier such as a capsule, tablet or powder. Alternatively, the ingestible carrier is a food product such as acidified milk, a yoghurt, a frozen food such as frozen yoghurt or ice cream, a gum, a candy, a milk powder, a milk concentrate, a cheese spread, a nutritional composition, a nutritional supplement, a cereal bar, a dressing or a beverage.

In one case the formulation is an infant food.

In some embodiments the formulation is in the form of a fermented food product.

The formulation may be in the form of a fermented milk product.

In some cases the carrier does not occur in nature.

The formulation may further comprise a protein and/or peptide, in particular proteins and/or peptides that are rich in glutamine/glutamate, a lipid, a carbohydrate, a vitamin, mineral and/or trace element.

The formulation may further comprise an adjuvant.

The formulation may further comprise a bacterial component.

The formulation may further comprise a drug entity.

The formulation may further comprise a biological compound.

The strains are in the form of freeze dried powder which is blended with food grade excipient, and filled into a format such as a sachet or capsule.

The strain of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives.

The amount of active ingredient in the medical composition may be at a level that will exercise the desired therapeutic effect.

The formulation may also include, a drug entity or a biological compound.

In addition a vaccine comprising the strains of the invention may be prepared using any suitable known method and may include a pharmaceutically acceptable carrier or adjuvant.

The introduction of probiotic organisms is accomplished by the ingestion of the micro-organism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit and is termed synbiotic.

It will be appreciated that the probiotic strains may be administered prophylactically or as a method of treatment either on their own or with other probiotic and/or prebiotic materials as described above. In addition, the bacteria may be used as part of a prophylactic or treatment regime using other active materials such as those used for treating related conditions especially those with an immunological involvement. Such combinations may be administered in a single formulation or as separate formulations administered at the same or different times and using the same or different routes of administration.

The strains of the invention may be formulated to facilitate controlled release such as a delayed release of the strain. For example, the formulation may be adapted to release the strain at a particular location in the gastrointestinal tract such as the small intestine or in the colon. To achieve such a controlled release the strain may be formulated in a capsule which has a coating which is adapted to release the strain at a particular location. A range of coatings are available to facilitate such controlled release. One such family of coatings are those available under the Trademark Eudragit.

Sleep disturbances are observed at any stage of the life. These disturbances are typically characterized by a decrease in the ability to initiate and maintain sleep, and by a reduced proportion of the deeper, more restorative sleep. Quality of life is substantially impaired in individuals suffering from those alterations.

Infant sleep normally changes over the first months of life to follow a diurnal rhythm with sleep lasting for a long unbroken period at night and, similarly, sleep states change from being equally distributed between REM (active) and NREM (quiet) sleep at birth to one third REM and two thirds NREM by 8 months of age. Any failure to successfully negotiate these changes in infancy can also have lasting effects on the sleep patterns of the child.

The most common sleep disturbances in infants and children are those related to wakefulness (i.e. either difficulties in settling at bedtime or failure to sleep through the night without interruptions). It has been estimated that these disturbances affect 15 to 35% of infants aged less than 24 months. Infant and child sleep disturbances inevitably lead to parental sleep disturbance and stress which may result inadequate child-parent interaction which in turn aggravates infant and child symptoms leading to a vicious circle.

At the other end of life normal aging is also accompanied by changes in the sleep quality, quantity, and architecture. Specifically, there appears to be a measurable decrease in the ability of the healthy elderly to initiate and maintain sleep, accompanied by a decrease in the proportion of the deeper, more restorative NREM sleep.

Sleep is particularly important in older people. Along with the physical changes that occur as we get older, changes to our sleep patterns are a part of the normal aging process. As people age they tend to have a harder time falling asleep and more trouble staying asleep than when they were younger. It is a common misconception that sleep needs decline with age. In fact, research demonstrates that our sleep needs remain constant throughout adulthood. Changes in the patterns of our sleep, "sleep architecture", occur as we age and this may contribute to sleep problems. Sleep occurs in multiple stages including dreamless periods of light and deep sleep, and occasional periods of active dreaming (REM sleep). The sleep cycle is repeated several times during the night and although total sleep time tends to remain constant, older people spend more time in the lighter stages of sleep than in deep sleep.

Many older adults, though certainly not all, also report being less satisfied with sleep and more tired during the day. Studies on the sleep habits of older Americans show an increase in the time it takes to fall asleep (sleep latency), an overall decline in REM sleep, and an increase in sleep fragmentation (waking up during the night) with age. The prevalence of sleep disorders also tends to increase with age. Research suggests that sleep disturbance among the elderly can in part be attributed to physical and psychiatric illnesses and the medications used to treat them.

In addition to changes in sleep architecture that occur as we age, other factors affecting sleep are the circadian rhythms that coordinate the timing of our bodily functions, including sleep. For example, older people tend to become sleepier in the early evening and wake earlier in the morning compared to younger adults. This pattern is called advanced sleep phase syndrome. The sleep rhythm is shifted forward so that 7 or 8 hours of sleep are still obtained but the individuals will wake up extremely early because they have gone to sleep quite early. The reason for these changes in sleep and circadian rhythms as we age is not clearly understood.

Environmental stressors can also be an issue. Exposure to stress negatively affects sleep and the sleep/wake cycle. For example, experiencing work-related stressors having low social support, or exposure to trauma/combat can all disrupt sleep and the sleep/wake cycle.

Clinical trials in sleep medicine cover a wide range of sleep-wake problems, and accordingly the selection of outcome measures in sleep medicine clinical trials needs to be tailored to the specific disorder under examination. The investigator needs to consider the relative merits choosing a self-report questionnaire versus a physiologic test. Surprisingly, the self-report measures are often more sensitive to treatment effects as compared with more expensive physiologic tests.

BRIEF DESCRIPTION OF THE DRAWINGS

The invention will be more clearly understood from the following description thereof, given by way of example only, in which.

DETAILED DESCRIPTION

A deposit of *B. longum* 1714™ strain was made at the National Collections of Industrial and Marine Bacteria Limited (NCIMB) Ferguson Building, Craibstone Estate, Bucksburn, Aberdeen, AB21 9YA, Scotland, UK on Nov. 5, 2009 and accorded the accession number NCIMB 41676.

WO2011/05853A, the entire contents of which are incorporated herein by reference, describes *B. longum* 1714™ strain—NCIMB 41676.

In the following examples NCIMB 41676 is tested in healthy humans, healthy humans involved in exams (a stressor that can lead to temporary disrupted sleep patterns) and in IBS patients who suffer from the chronic effects of gastrointestinal disturbance with frequently reported effects on sleep.

Example 1—Effect of *B. longum* 1714™ on Sleep in Healthy Humans 42 subjects were recruited from the general population to take part in an on-line study. Subjects were provided in a capsule format containing $1\times10^9$ colony-forming units *B. longum* 1714™ for weeks. Subjects were asked to take 1 capsule per day for the duration of the study and complete an on-line questionnaire.

In the on-line study, participants were asked the following question every week:

Reflecting over the last week how would you rate your sleep quality? (0=very bad, 9=very good)

Figure 1:
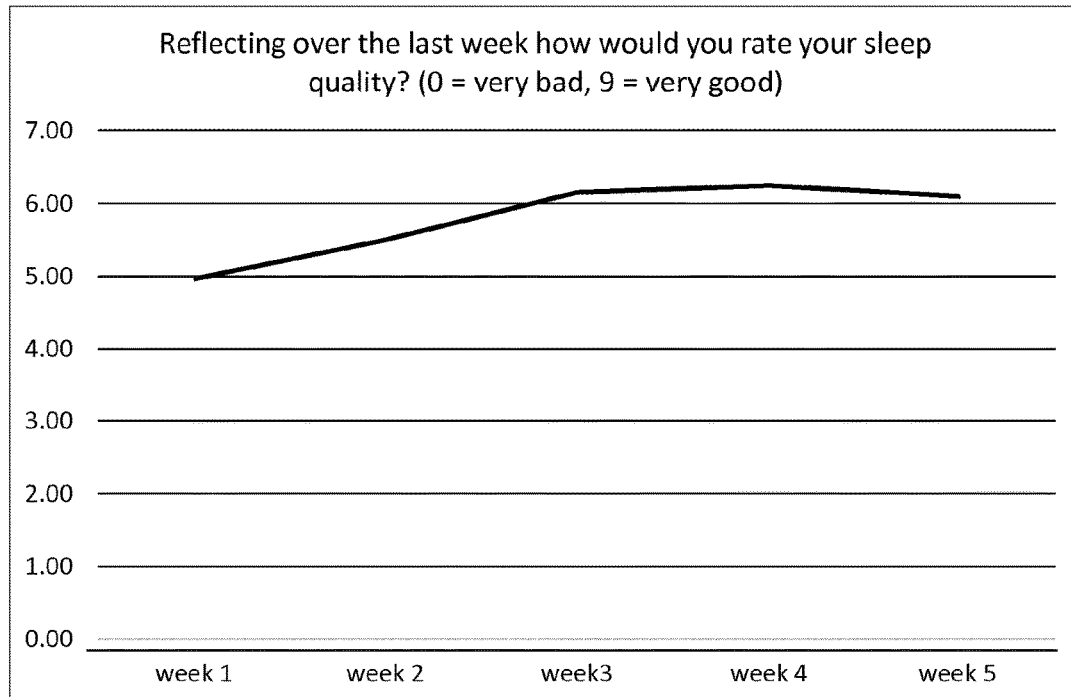
FIG. 1 is a graph illustrating the effect of *B. longum* 1714™ strain on sleep in an on-line study with healthy volunteers.

The results of this study showed that sleep quality increased progressively over the course of the study (FIG. 1). This work shows that *B. longum* 1714™ strain increased sleep quality over the course of the study.

The invention is not limited to the embodiments hereinbefore described which may be varied in detail.

Figure 2:
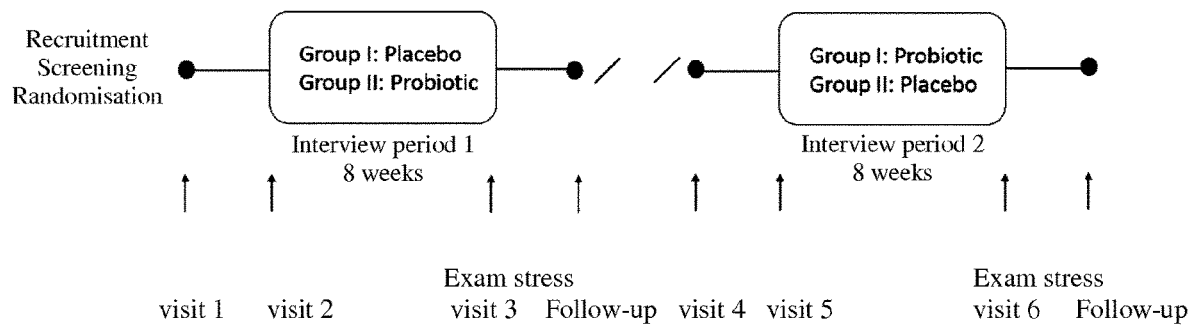
FIG. 2 is a study flow diagram of double-blinded, randomised, placebo-controlled, cross-over study of *Bifidobacterium longum* 1714 in a chronic exam stress model in healthy individuals.

Example 2—A Double-Blinded, Randomised, Placebo-Controlled, Cross-Over Study: *Bifidobacterium longum* 1714™ Strain Improves Sleep During Chronic Exam Stress in Healthy Individuals We saw an improvement in sleep quality in the general healthy population (FIG. 1) therefore we assessed sleep quality after *Bifidobacterium longum* 1714 strain administration in healthy students in a chronic stress model in the controlled setting of a double-blinded, randomised, placebo-controlled, cross-over study. This human study utilising the naturalistic stressor, exam stress, was performed to determine the usefulness of the *Bifidobacterium longum* 1714 as a means to improve sleep in a model of chronic stress (university exam stress of 3 week period). The study outline is described in FIG. 2. Other studies have shown that sleep quality is reduced by exams in students. The trial design used is a valid approach to assess sleep quality in chronically stressed situations.

Study population included 20 healthy male and female student volunteers aged between 18-24 years. g*Power was utilised for power calculations, with an a-error probability (false positive) of 0.05, a power of 80% and effect sizes of 0.3. The criteria for inclusion were: 1) able to give written informed consent; 2) age between 18 and 24 years; and 3) in generally good health as determined by the investigator. The exclusion criteria were: 1) less than 18 and greater than 40 years of age; 2) have a significant acute or chronic coexisting illness, immunological, psychiatric, neurodevelopmental disorders, immunological, metabolic disorders, or any condition which contraindicates, in the investigators judgement, entry to the study; 3) have a condition or taking a medication that the investigator believes would interfere with the objectives of the study, pose a safety risk or confound the interpretation of the study results; all psychoactive medications, laxatives, enemas, antibiotics, anti-coagulants, over-the counter non-steroidal anti-inflammatories (NSAIDS) (subjects should have a wash-out period of 4 weeks); 4) Current prebiotic or probiotic use; 5) Females who are pregnant or planning a pregnancy; 6) Are a current or past smoker; and 7) Have a malignant disease or any concomitant end-stage organ disease.

The products administered during intervention were either probiotic B. longum 1714 ($1 \times 10^9$ CFU/day) in excipient or placebo consisting only excipient in capsule format.

Pittsburgh Sleep Quality Index (PSQI) questionnaire was administered at baseline and after the feeding phase to assess sleep quality over the prior month. The PSQI is a self-report measure comprised of 19 items which are designed to measure seven key components indicating problematic or non-problematic sleep; sleep latency (time to fall asleep), sleep duration, sleep efficiency, sleep disturbances, subjective sleep quality, use of sleep medication, and daytime dysfunction due to sleep disturbance. Scores on each component are combined to give a global score with >5 indicating significant disturbance of sleep quality during the prior month.

Figure 3:
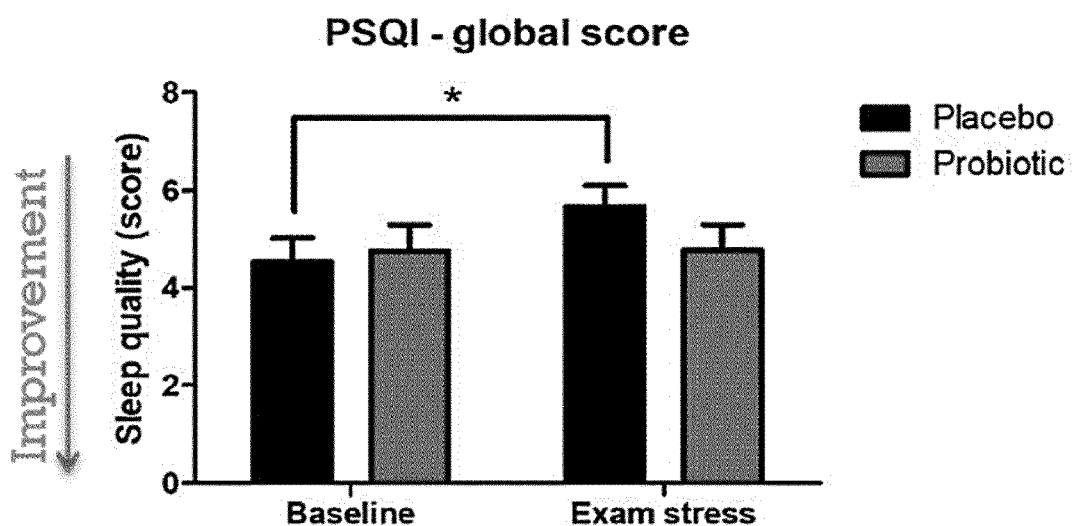
FIG. 3 is a graph of the global score of sleep quality measured by Pittsburgh Sleep Quality Index (PSQI) at baseline and during exam stress comparing the effect of probiotic and placebo administration.

The overall sleep quality reflected in the global score of PSQI at baseline (before intervention) were similar between probiotic and placebo groups. After 8 weeks of intervention, during exam stress period, the PSQI was measured again to compare the effect of probiotic and placebo administration on sleep quality. Only placebo group had worsened sleep quality (higher score) while there was no change in sleep quality in the probiotic group under exam stress (FIG. 3).

Figure 4A:
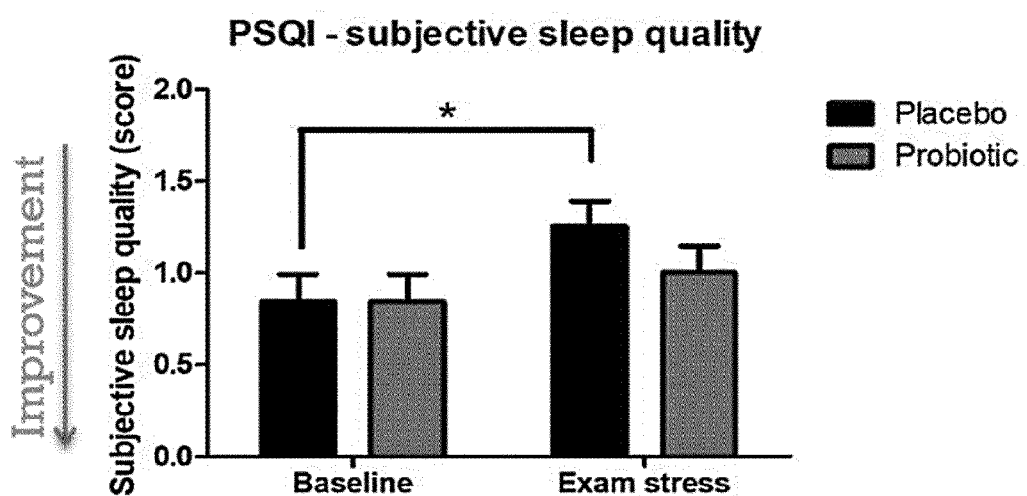
FIGS. 4(*a*) and 4(*b*) are graphs of the sub-scores of the components within PSQI that measure subjective sleep quality (FIG. 4(*a*)) and sleep latency (FIG. 4(*b*)) at baseline and during exam stress comparing the effect of probiotic and placebo administration.
Figure 4B:
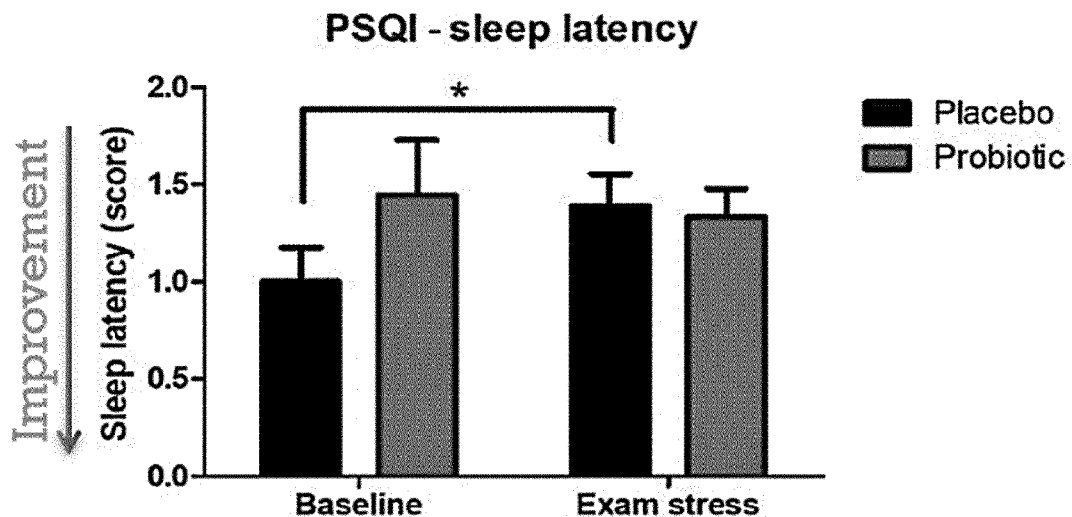

This result corresponds to those of the sub-scores of the components within PSQI that measure subjective sleep quality and sleep latency (FIGS. 4(a) and (b)). Only placebo group had worsened subjective sleep quality and sleep latency (statistically significant higher scores) under exam stress compared to baseline.

Figure 5A:
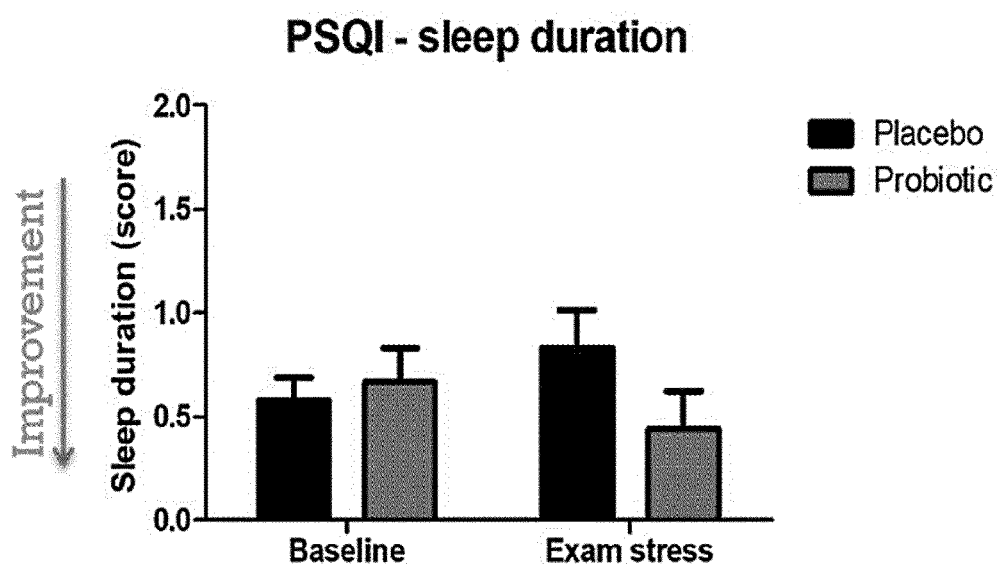
FIGS. 5(*a*) and 5(*b*) are graphs of the sub-score of the component within PSQI that measures sleep duration at baseline and during exam stress comparing the effect of probiotic and placebo administration (FIG. 5(*a*)) and change in sleep duration before and after intervention (FIG. 5(*b*))
Figure 5B:
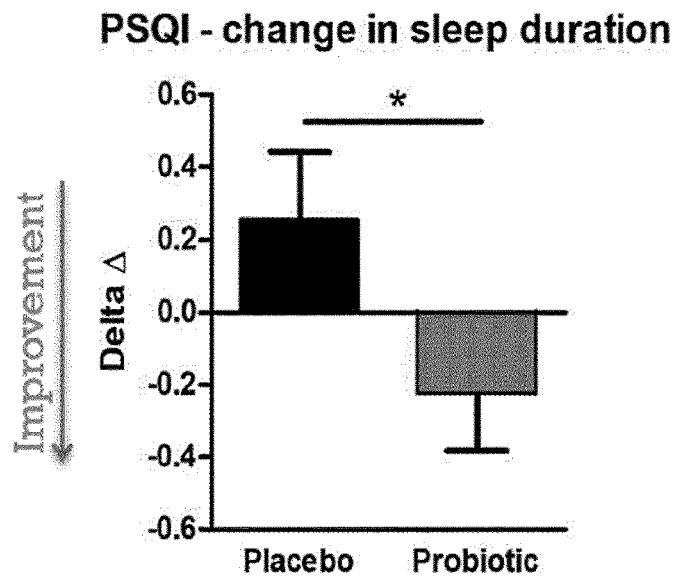

Sleep duration as determined by the following question 'How many hours of actual sleep did you get at night?' were similar in probiotic and placebo groups at baseline. However, following 8 weeks of feeding with the 1714 strain, there was an increase in subjective assessment of sleep duration in the probiotic group compared to placebo (FIGS. 5(a) and (b)). As graphed, a lower score reflects an improvement in sleep duration which is based on the correct analysis of the PSQI questionnaire.

Taken together these results show that exam stress period affects sleep quality as shown in higher global PSQI score and higher sub-scores of subjective sleep quality, sleep latency and sleep duration suggestive of loss of sleep efficiency in placebo group; and administration of *Bifidobacterium longum* 1714 for 8 weeks pre-exam stress improved sleep duration, efficiency and prevented the negative effect of the stressful period on sleep quality.

Example 3—An Open Label Irritable Bowel Syndrome (IBS) Study: A Combination B. longum Product Shows Improvement in Sleep Quality as Measured by the Pittsburgh Sleep Quality Index in IBS Patients A human open label study was performed as follows to investigate the effect of a combination of B. longum 1714™ and B. longum 35624® strain in adults with irritable bowel syndrome (IBS). The effects seen in the healthy population (examples 1 and 2) with the 1714™ strain were further assessed in combination with the 35624® strains using the Pittsburgh Sleep Quality Index (PSQI).

Figure 6:
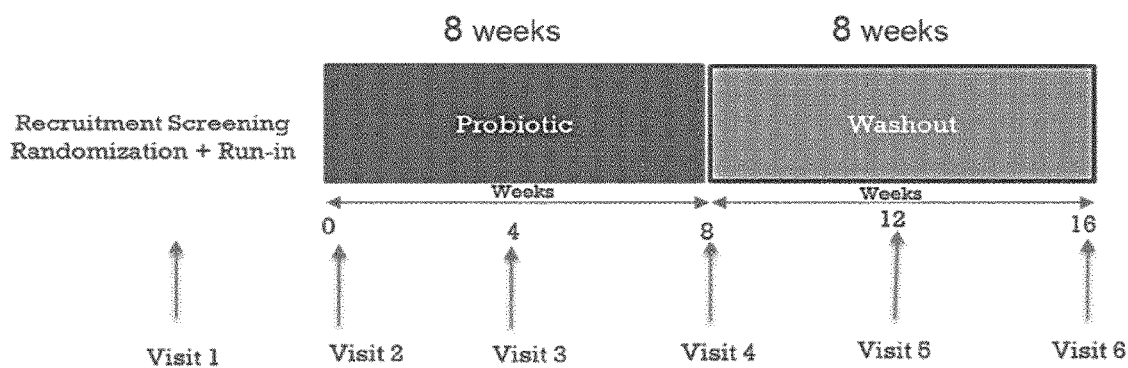
FIG. 6 is a schematic diagram of an open label combo IBS study schematic.

The clinical protocol for this trial was as follows:

Forty female subjects aged 18-55 years were recruited with IBS, diagnosed by Rome III criteria, and mild to moderate anxiety and/or depression as determined by the Hospital Anxiety and Depression scale (HADs). Subjects who had a psychiatric diagnosis other than anxiety or depression, a major inflammatory disorder or were on anti-depressants, anxiolytics or antipsychotics in the last 6 months were excluded. The 'COMBO' ($5 \times 10^8$ CFU/day B. longum 35624+$1 \times 10^9$ CFU/day B. longum 1714), sachet format with maltodextrin and a flowability agent such as silicon dioxide was taken for 8-weeks, followed by an 8 week washout (FIG. 6). The PSQI was measured at 0, 4, 8, 12 and 16 weeks. Sleep quality was assessed through a modified PSQI designed to measure sleep quality and disturbance over the past month in clinical populations as it has acceptable reliability and validity (Buysse et al., 1989). The PSQI is a 19-item self-report measure assessing sleep quality across seven domains. Each of the sleep components yields a score ranging from 0 to 3, with 3 indicating the greatest dysfunction. The sleep component scores are summed to yield a total score ranging from 0 to 21 with the higher total score (referred to as global score) indicating worse sleep quality. In distinguishing good and poor sleepers, a global PSQI score>5 yields a sensitivity of 89.6% and a specificity of 86.5%. 1 (Buysse et al., 1991; Herman et al., 2002; Fillingim et al.; 2011, Porto et al., 2011). We used this >5 global PSQI cut off to look at a subpopulation of our IBS patients who have poor sleep quality. Subjective sleep quality is scored as follows 'very good' (0,) 'fairly good' (1), 'fairly bad' (2) 'very bad' (3).

Figure 7A:
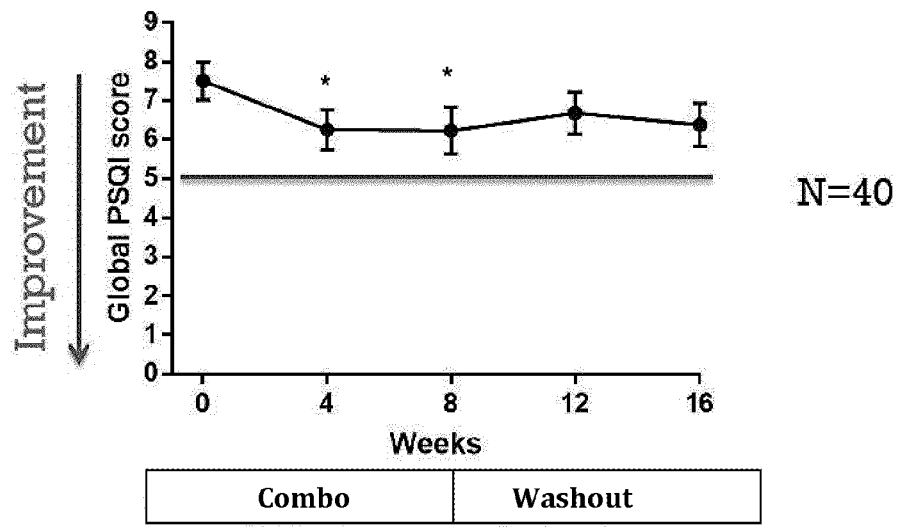
FIGS. 7(*a*) and 7(*b*) are plots of global PSQI score for the IBS patients (FIG. 7(*a*)) and IBS patients (PSQI over 5) (FIG. 7(*b*)) before and after combo treatment.
Figure 7B:
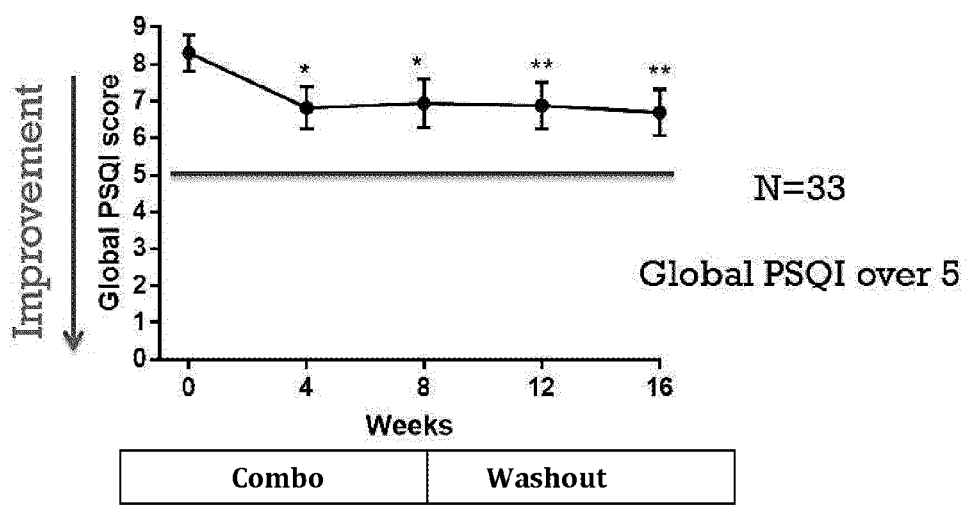
Figure 8A:
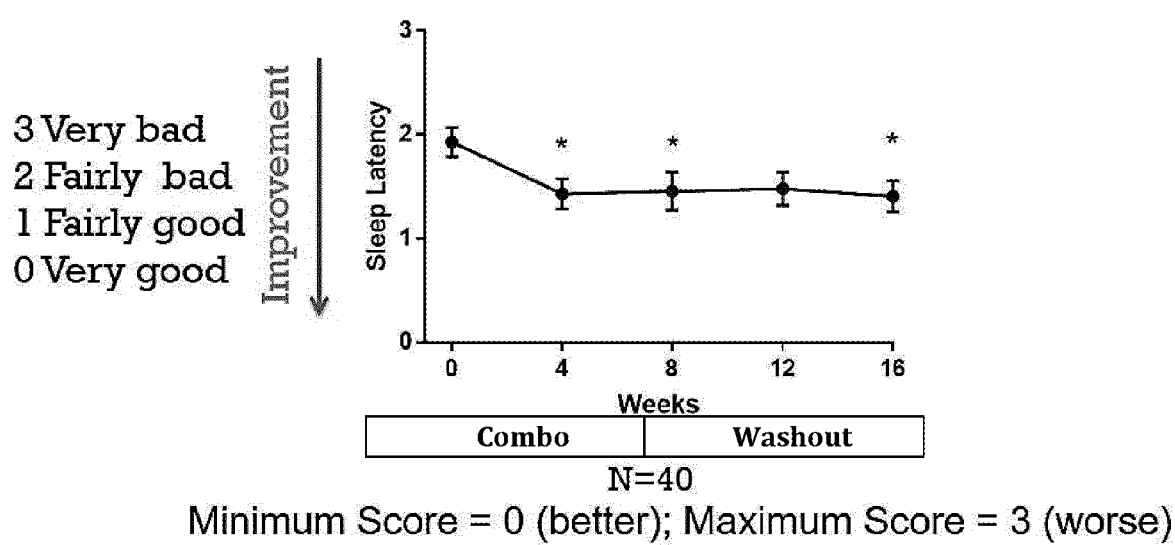
FIGS. 8(*a*) and 8(*b*) are plots of subjective sleep latency for the IBS patients (FIG. 8(*a*)) and IBS patients (PSQI over 5) (FIG. 8(*b*)) before and after combo treatment.
Figure 8B:
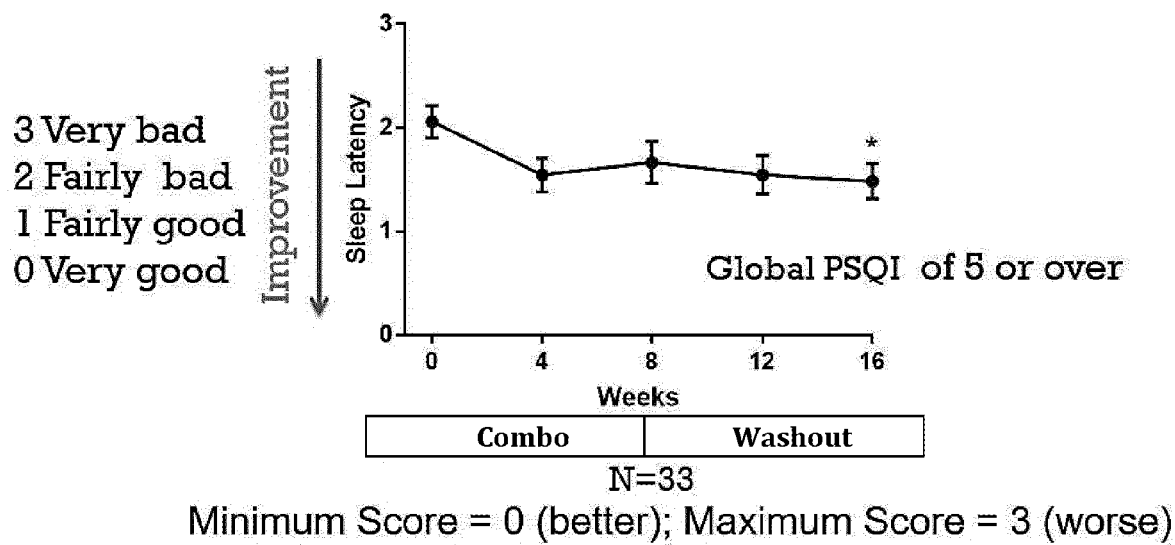
Figures 9A, 9B:
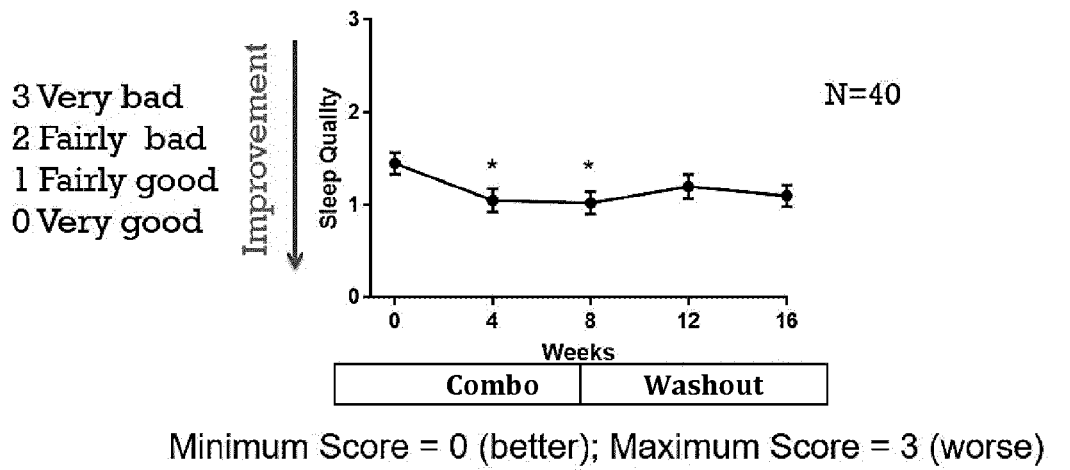
FIGS. 9(*a*) and 9(*b*) are a plot and table, respectively, of subjective sleep quality for the IBS patients before and after combo treatment.
Figures 10A, 10B:
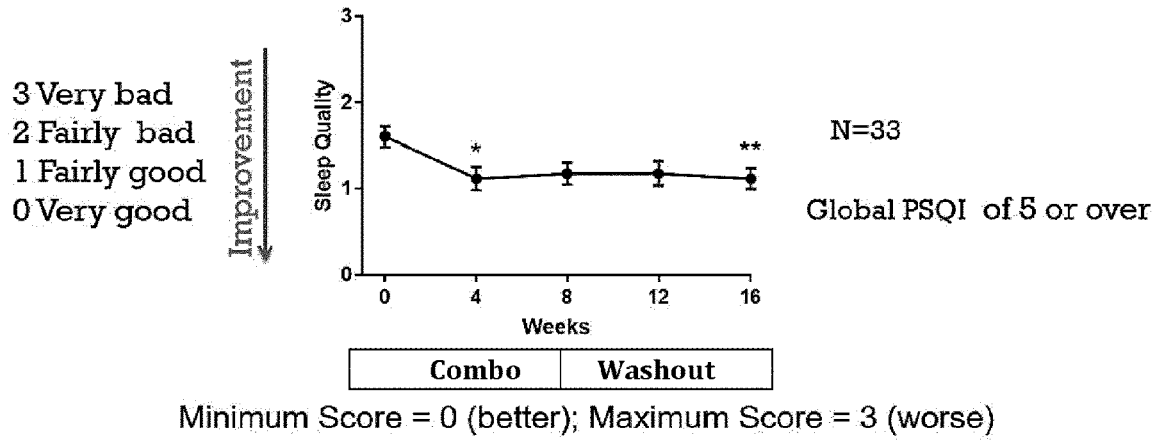
FIGS. 10(*a*) and 10(*b*) are a plot and table, respectively, of subjective sleep quality for the IBS patients (PSQI over 5) before and after combo treatment.

The daily ingestion of the combo product significantly decreased PSQI global scores at week 4 and week 8 (FIG. 7(a)). A decrease in PSQI global score indicates an improvement in sleep quality. When looking at a sub group of our IBS patients who had poor sleep quality (>5 global PSQI) the combo significantly decreased PSQI global scores at all time points even those post feeding (FIG. 7(b)). The global PSQI score is the sum of seven component scores (sleep disturbance, overall sleep quality, sleep latency (time to fall asleep), duration of sleep, daytime dysfunction due to sleepiness, sleep efficiency, and need for medicines to sleep). Among them, the combo significantly decreased the PSQI-sleep latency score at week 4 and week 8, and 8 weeks post feeding (FIG. 8(a)). Again, when we looked at a sub population of "bad sleepers" we saw a decrease in PSQI-sleep latency at 8 weeks post feeding (FIG. 8(b)). Another notable result was that when subjects were asked the question 'during the past month, how would you rate your sleep quality overall?), the results showed that administration of the Combo product significantly improved sleep quality in agreement with the PSQI global score. Subjective sleep quality scores improved from baseline to the end of the intervention (8 weeks), in the combo group and maintained their effect after feeding had stopped (16 weeks) (FIG. 9(a)). When looking at percentage of the different categories of sleepers the combo treatment increased the number of patients describing their sleep as 'good' and decreasing the number of subjects who had 'fairly bad' sleep and this is maintained even after the feeding has stopped (FIG. 9(b)). We also analysed a sub group of IBS patients who had reported that they had 'bad' sleep at baseline, and this was reflected in a global score of PSQI of greater than 5. Subjective sleep quality scores improved from baseline to the end of the intervention (8 weeks) in this group (global PSQI score of over 5) and maintained their effect after feeding had stopped (16 weeks) (FIG. 10(a)). When looking at percentage of the different categories of sleepers the combo treatment increased the number of patients describing their sleep as 'fairly good' and decreasing the number of subjects who had 'fairly bad' sleep and this is maintained even after the feeding has stopped (FIG. 10(b)).

In this IBS study 33 of the 40 patients had a global PSQI score of over 5 and have so been characterised as bad sleepers which agrees with the literature which shows that IBS patients have poor sleep quality. After combo administration there was a significant improvement in sleep quality as measured by the PSQI in these IBS patients and this effect is maintained 8 weeks after the combo administration.

The beneficial effect of combo product on sleep quality is indicative of the potential benefits of *Bifidobacterium longum* 1714™ strain for improving sleep quality, especially in IBS patients.

The effect of 1714™ strain on sleep quality was assessed in healthy human subjects, and chronically stressed healthy subjects and IBS patients and it has shown benefit in all three instances.

The invention is not limited to the embodiments hereinbefore described.

REFERENCES

BRAVO J A, FORSYTHE P, CHEW M V, ESCARAVAGE E, SAVIGNAC H M, DINAN T G, ET AL. 2011 Ingestion of Lactobacillus strain regulates emotional behavior and central GABA receptor expression in a mouse via the vagus nerve. *Proc Natl Acad Sci USA.;* 108(38):16050-5.
BUYSSE D J, REYNOLDS C F, MONK T H, BERMAN S R, KUPFER D J 1989 The Pittsburgh Sleep Quality Index: a new instrument for psychiatric practice and research. Psychiatry Res. May; 28(2): 193-213.
BUYSSE D J, REYNOLDS C F 3RD, MONK T H, HOCH C C, YEAGER A L, KUPFER D J. 1991 Quantification of subjective sleep quality in healthy elderly men and women using the Pittsburgh Sleep Quality Index (PSQI) Sleep. August; 14(4):331-8.
DINAN T G, STANTON C, CRYAN J F. 2013 Psychobiotics: a novel class of psychotropic. *Biol Psychiatry.;* 74(10):720-6,
FILLINGIM R B, OHRBACH R, GREENSPAN J D, KNOTT C, DUBNER R, BAIR E, BARAIAN C, SLADE G D, MAIXNER W. 2011 Potential psychosocial risk factors for chronic TMD: descriptive data and empirically identified domains from the OPPERA patient-control study. J Pain.; 12:T46-T60.
HERMAN C R, SCHIFFMAN E L, LOOK J O, RINDAL D B 2002 The effectiveness of adding pharmacologic treatment with clonazepam or cyclobenzaprine to patient education and self-care for the treatment of jaw pain upon awakening: a randomized clinical trial. J Orofac Pain.; 16:64-70.
INSTITUTE OF MEDICINE (US) COMMITTEE ON SLEEP MEDICINE AND RESEARCH; COLTEN H R, ALTEVOGT B M, EDITORS. 2006 Sleep Disorders and Sleep Deprivation: An Unmet Public Health Problem. Washington (DC): *National Academies Press (US).*
PINTO-SANCHEZ, M. I., HALL, G. B., GHAJAR, K., NARDELLI, A., BOLINO, C., LAU, J. T., MARTIN, F. P., COMINETTI, O., WELSH, C., RIEDER, A., TRAYNOR, J., GREGORY, C., DE PALMA, G., PIGRAU, M., FORD, A. C., MACRI, J., BERNER, B., BERGONZELLI, G., SURETTE, M. G., COLLINS, S. M., MOAYYEDI, P. & BERCIK, P. 2017. Probiotic *Bifidobacterium longum* NCC3001 Reduces Depression Scores and Alters Brain Activity: a Pilot Study in Patients With Irritable Bowel Syndrome. *Gastroenterology.*
PORTO F, D E LEEUW R, EVANS D R, CARLSON C R, YEPES J F, BRANSCUM A, OKESON J P. 2011 Differences in psychosocial functioning and sleep quality between idiopathic continuous orofacial neuropathic pain patients and chronic masticatory muscle pain patients. J Orofac Pain.; 25:117-124

The invention claimed is:

1. A method of treating a mammalian subject, the method comprising orally administering a formulation comprising an excipient and a therapeutically effective amount of *Bifidobacterium longum* strain NCIMB 41676 to the subject, wherein the formulation improves sleep in the subject as measured by a decrease in amount of time to fall asleep, an increase in sleep duration, a decrease in sleep disturbance, a decrease in daytime dysfunction due to sleep disturbance, or a combination thereof, compared to a corresponding mammalian subject orally administered with only the excipient.

2. The method of claim 1, wherein the *Bifidobacterium longum* strain is in the form of viable cells.

3. The method of claim 1, wherein the *Bifidobacterium longum* strain is in the form of non-viable cells.

4. The method of claim 1, wherein the subject is a human.

5. The method of claim 1, wherein the formulation further comprises a prebiotic.

6. The method of claim 1, wherein the formulation further comprises an ingestable carrier.

7. The method of claim 1, wherein the formulation is in the form of a capsule, a tablet or a powder.

8. The method of claim 1, wherein the formulation is in the form of a food product.

9. The method of claim 1, wherein the formulation comprises a protein, a peptide, or a combination thereof.

10. The method of claim 5, wherein the *Bifidobacterium longum* strain is present in the formulation in an amount of more than $10^6$ cfu.

11. The method of claim 5, wherein the *Bifidobacterium longum* strain is present in the formulation in an amount of from $10^7$ to $10^{10}$ cfu.

12. The method of claim 5, wherein the *Bifidobacterium longum* strain is present in the formulation in an amount of from $10^8$ to $10^9$ cfu.

13. The method of claim 5, wherein the formulation comprises an adjuvant.

14. The method of claim 5, wherein the formulation further comprises a drug entity or a biological compound.

15. The method of claim 1, wherein the subject is a baby.

16. The method of claim 1, wherein the subject is an elderly person.

17. The method of claim 1, wherein the improvement in sleep is determined according to the Pittsburgh Sleep Quality Index (PSQI).

18. The method of claim 8, wherein the food product comprises an acidified milk, a yoghurt, a frozen food, a gum, a candy, a milk powder, a milk concentrate, a cheese spread, a nutritional composition, a nutritional supplement, a cereal bar, a dressing or a beverage.

19. The method of claim 9, wherein the peptide, the protein, peptide, or the combination thereof are rich in glutamine/glutamate, a lipid, a carbohydrate, a vitamin, a mineral, a trace element, or a combination thereof.

20. The method of claim 1, wherein the *Bifidobacterium longum* strain is in the form of a powder blended with a food grade excipient, the formulation being in the form of a sachet or a capsule.

21. The method of claim 1, wherein the formulation is administered to the subject in the form of one capsule per day.

22. A method of treating a subject, the method comprising orally administering a formulation comprising a prebiotic and a therapeutically effective amount of *Bifidobacterium longum* strain NCIMB 41676 to the subject, wherein the subject is a human and the formulation improves sleep in the subject as measured by Pittsburgh Sleep Quality Index (PSQI).

23. The method of claim 22, wherein the *Bifidobacterium longum* strain is present in the formulation in an amount of from $10^7$ to $10^{10}$ cfu.

24. The method of claim 22, wherein the prebiotic comprises fructose, xylose, soya, galactose, glucose, mannose, or a combination thereof.

25. A method of treating a mammalian subject, the method comprising orally administering a formulation comprising an excipient and a therapeutically effective amount of *Bifidobacterium longum* strain NCIMB 41676 to the subject, wherein the formulation improves sleep in the subject as measured by a decrease in amount of time to fall asleep, an increase in sleep duration, a decrease in sleep disturbance, a decrease in daytime dysfunction due to sleep disturbance, or a combination thereof compared to a corresponding mammalian subject orally administered with only the excipient, wherein the formulation is in the form of a capsule, a tablet, a powder, or a food product.

* * * * *